United States Patent [19]
Edwards et al.

[11] Patent Number: 5,942,215
[45] Date of Patent: Aug. 24, 1999

[54] ANTIPERSPIRANT COMPOSITION

[75] Inventors: Christopher John Carruthers Edwards, Leeds; Isabelle Claire Helen Marie Esser, Port Sunlight, both of United Kingdom

[73] Assignee: Helene Curtis, Inc., Chicago, Ill.

[21] Appl. No.: 08/959,864

[22] Filed: Oct. 29, 1997

[30] Foreign Application Priority Data

Oct. 30, 1996 [GB] United Kingdom ............... 9622580

[51] Int. Cl.$^6$ ............... A61K 7/32; A61K 7/00
[52] U.S. Cl. ............... 424/65; 424/66; 424/67; 424/68; 424/400; 424/401
[58] Field of Search ............... 424/65, 66, 67, 424/68, 400, 401

[56] References Cited

U.S. PATENT DOCUMENTS 5,654,362  8/1997  Schulz, Jr. et al. ............... 524/862

FOREIGN PATENT DOCUMENTS

97/44010  11/1997  WIPO .
98/00097  1/1998  WIPO .

OTHER PUBLICATIONS

International Search Report Application No. PCT/EP 97/06014 dated Apr. 2, 1998.

*Primary Examiner*—Shelley A. Dodson
*Attorney, Agent, or Firm*—Matthew Boxer

[57] ABSTRACT

An antiperspirant stick composition suitable for topical application to human skin, comprising:

i. an effective amount of an antiperspirant astringent;
ii. a volatile silicone;
iii. a structurant; and
iv. a cross-linked or partially cross-linked non-emulsifying siloxane elastomer.

6 Claims, No Drawings

ANTIPERSPIRANT COMPOSITION

The invention relates to antiperspirant compositions suitable for topical application to human skin, particularly solid compositions suitable for use as a cosmetic stick together with a stick holder.

The deodorant and antiperspirant market is dominated with products based on aluminium or zirconium salts which are intended to prevent, or at least control, perspiration at the skin surface, particularly on the underarm, whilst often simultaneously providing a perceived degree of deodorancy.

Various physical forms of anti-perspirant compositions are known, for example aerosol, lotion, or solid form.

When the antiperspirant is provided as a solid composition for use in "stick" form, it is known to incorporate the active components which may be present in the composition, such as for example the aluminium or zirconium salt and the other components of the composition, in a cosmetically acceptable vehicle comprising largely silicone oils (whether volatile or non-volatile), and a matrix of long chain fatty alcohols which act as a structurant.

For example, in U.S. Pat. No. 4,126,679 (Armour-Dial), there is described the possibility of making solid stick antiperspirant compositions comprising powdered astringent metallic salts, suspended in a matrix comprising volatile silicone oils, and 15 to 70% alcohols selected from long-chain water insoluble aliphatic alcohols having 16–22 carbon atoms in the chain.

EP-B-117,070 (Procter & Gamble) describes a solid stick antiperspirant composition, which comprises 5 to 20% of a long chain fatty alcohol having 8 to 18 carbon atoms in its chain, 35 to 55% of a volatile polydimethyl silicone, 10 to 70% of an astringent antiperspirant salt, and 1 to 3% by weight of the total long chain fatty alcohol level of the composition of an additional long chain fatty alcohol selected from $C_{20}$–$C_{26}$ fatty alcohols, or mixtures thereof.

A problem with existing solid stick formulations in general is poor sensory properties as perceived by the user. Typically, the sticks are perceived as being wet and/or greasy. The wet or greasy feel can be a result of the seepage of silicone oils out of the matrix, with a subsequent loss of beneficial properties. It is already known that, generally speaking, silicone oils and long chain fatty alcohols in solid form are not compatible, there being a tendency for the long chain alcohol to "press" the silicone oils out of the matrix.

According to the invention there is provided an antiperspirant stick composition suitable for topical application to human skin, comprising:

i. an effective amount of an antiperspirant astringent;
ii. a volatile silicone;
iii. a structurant; and
iv. a cross-linked or partially cross-linked non-emulsifying siloxane elastomer.

The cross-linked or partially cross-linked non-emulsifying siloxane elastomer comprises from 0.1 to 20% of the composition, preferably from 0.1 to 10% and more preferably from 0.1 to 5% of the composition according to the invention.

Preferably, the crosslinked siloxane elastomer is formed from the hydrosilation of vinyl silicone fluids by hydrosiloxane or MQ hydride fluids.

More preferably, the non-emulsifying siloxane elastomer is a dimethicone/vinyldimethicone cross polymer.

Suitably, the antiperspirant astringent comprises 1–35% by weight of the composition. More preferably the antiperspirant astringent comprises 5–30% of the composition.

The structurant, which is preferably a long chain water insoluble aliphatic alcohol, comprises up to 40% of the composition. Fatty alcohols suitable for use as structurants are those having around 12–22 carbon atoms.

The volatile silicone is preferably a linear or cyclic volatile silicone comprising from 3 to 9 and preferably from 4–6 silicon atoms. The volatile silicone comprises from 1 to 85% and preferably from 5–70% of the composition.

In a preferred embodiment, the invention provides an antiperspirant composition suitable for topical application to the human skin, comprising:

i. 15–25% by weight of the total composition of an antiperspirant astringent;
ii. 50–60% by weight of the total composition of a linear or cyclic volatile silicone;
iii. 5 to 30% by weight of the total composition of long chain water insoluble aliphatic alcohols having 16–22 carbon atoms in the chain; and
iv. 0.1 to 20% by weight of a vinyldimethicone/dimethicone cross polymer elastomer.

We have surprisingly found that by the use of cross-linked or partially cross-linked non-emulsifying siloxane elastomers in combination with a volatile silicone it is possible to produce an antiperspirant stick composition which has improved and attractive cosmetic characteristics expected of such sticks.

One parameter that has to be very closely controlled with stick formulations is the hardness of the stick. This is important not only because it determines the storage properties of the stick, in particular the resistance of the stick to degradation caused by temperature extremes, but also because it determines the deposition of antiperspirant composition that occurs when the stick is used for a given application stroke.

Viewed against the above mentioned background of prior art, it has been found that cosmetic sticks with desirable hardness, pay off and skin feel can be made using siloxane elastomers as herein defined in combination with fatty alcohols.

Compositions according to the invention not only have useful hardness properties at ambient temperatures, but they also enable the antiperspirant composition to be formulated easily. It has also been discovered that stick formulations according to the invention tend to show a reduced tendency towards "flaking" and have an improved dry non-greasy feel compared to other antiperspirant formulations in which the carrier comprises, for example, volatile silicone in the absence of an elastomer.

An underarm stick of enhanced properties can be achieved through incorporation of a cross-linked or partially cross-linked non-emulsifying siloxane elastomer in combination with an oily material, preferably a volatile silicone, into the stick. A principal advantage of the composition is that when the elastomer is swollen in the volatile silicone (e.g. cyclomethicone), the resultant material (hereinafter referred to as the "gel") prevents seepage of volatile silicone which can result in a greasy feel. Furthermore, the elastomer thickens the cyclomethicone. The aesthetics of the resultant stick product are superior to those of known products.

The siloxane elastomers are crosslinked or partially crosslinked, entangled, viscoelastic polymer networks, preferably made by the Pt catalysed reaction known as hydrosilation of vinyl silicone fluids by either hydrosiloxane fluids or highly branched MQ hydride fluids. Control of the stoichiometry and type of the vinyl silicone fluid and the silanic crosslinker controls the properties of the cured networks. Additional vinyl reactants such as vinylalkenes can be introduced in the reactive medium to further modify the silicone network. The choice of the reaction solvent(s) is also a means to modify the properties of the resultant gels as a certain amount, which can easily be controlled, is entrapped into the polymeric network giving different properties such as skin feel. The average molecular weight of the silicone elastomers is between 10,000 and 40 million and preferably between 10,000 and 20 million.

Typically the crosslinked siloxane polymeric networks are swollen substantially by oily materials, preferably silicone fluids such as cyclomethicone and/or dimethicone, to form gels, the characteristics of the gel being dependant on the degree of crosslinking. The resultant gels are not weakened by normal shearing (e.g at 2000 rpm), heat or rubbing on the skin and contain between 0.1 and 50% of crosslinked silicone polymeric network i.e. elastomer.

Illustrative examples of gels are materials with the CTFA name of cyclomethicone dimethicone/vinyl dimethicone crosspolymer containing about 0.1 to 50%, preferably 1 to 20% and more preferably 1% to 8% of the dimethicone/vinyl dimethicone crosspolymer (elastomer) and known as KSG-15 ex Shin-Etsu. Other such suitable crosslinked siloxane elastomers and gels are available from Witco Corporation, Dow Corning and General Electric.

The composition according to the invention comprises an antiperspirant astringent. Examples of suitable astringents include aluminium salts, zirconium salts, aluminium and/or zirconium complexes, for example aluminium halides, aluminium hydroxy halides, zirconyl oxyhalides, zirconyl hydroxyhalides, and mixtures thereof. Useful zirconium salts include zirconium hydroxy-chloride and zirconium oxychloride. Other generally used astringents will be known to those skilled in the art. Preferred astringents include AAZG (Activated Aluminium Zirconium Glycine), ZAG (Zirconium Aluminium Glycine), and AACH (Activated Aluminium Chorohydrate).

Examples of suitable volatile silicones include polydimethyl cyclosiloxanes, having a viscosity of less than 10 $mm^2s^{-1}$, examples of which are DOW CORNING fluids 344 and 244 (tetramer) and DOW CORNING Fluids 245 and 345 (pentamer). Other suitable silicones include hexamethyldisiloxane having a viscosity of not more than 0.65 $mm^2s^{-1}$, for example DOW CORNING 200 Fluid, which has a viscosity of 0.65 $mm^2s^{-1}$ as determined in accordance with the method provided in the data sheets provided by the manufacturer on these compounds.

The preferred volatile silicones are the cyclic forms.

The composition according to the invention can optionally comprise other ingredients, in addition to those already identified, depending on the nature and form of the finished product.

Examples of other ingredients which can optionally be present in the composition according to the invention include:

emollients, such as non-volatile silicones, hydrocarbons or mineral oils;

non-volatile silicones include polydimethylsiloxane having a viscosity in excess of 5 $mm^2s^{-1}$, for example, from 50 to 1000 $mm^2s^{-1}$, such as DOW CORNING 200 Fluids (standard viscosities 50–1000 $mm^2s^{-1}$). Other useful emollients include PEG 400 distearate, and ethylene oxide and/or propylene oxide condensation products having the following formula:

$$RO(C_2H_4O)_a(C_3H_6O)_bH$$

where R is either hydrogen or a hydrocarbon chain having from about 2 to 20 carbon atoms, and a and b are each from about 0 to 35 and a+b is from about 5 to 35. One example of such an emollient is Fluid AP or Ethylflo, a condensate of about 14 moles of propylene acid with about 1 mole of butyl alcohol sold by Union Carbide;

still further emollients suitable for use in the present solid stick compositions include fatty acid and fatty alcohol esters and water insoluble ethers;

thickeners, such as clays, for example Bentone 38; silica, for example Aerosil 200;

skin feel improvers, such as talc and finely divided polyethylene, an example of which is ACUMIST B18;

cosmetically acceptable vehicles, such as anhydrous ethanol and other emollients;

perfumes;

preservatives; and other cosmetic adjuncts conventionally employed in stick deodorant products.

A preferred optional component includes a wax such as, castor wax, Synchrowax HRC, Carnaubau, beeswax, silicone waxes and glycerol monostearate and mixture thereof at levels of from about 1 to 10% preferably 2 to 8%. If present, the wax is believed to enhance structural stability of the composition in the molten state.

The ingredients which can optionally be present in the composition can conveniently form the balance of the composition.

The composition according to the invention can take the form of a solid product suited to or adapted for topical application to human skin. One convenient form of the composition according to the invention is a solid stick, usually contained in a suitable holder or dispenser to enable it to be applied to the area of the skin, particularly the underarm, where control of perspiration and deodorancy is required.

The invention also provides for the use of a solid stick antiperspirant composition, in accordance with the invention, as herein defined, in perspiration control, following topical application to human skin.

EXAMPLES

The invention is further illustrated by the following examples.

Comparative Example

|  | wt % |
|---|---|
| Volatile Silicone (DC345) | 52.80 |
| AZAG (Active) | 24.00 |
| Stearyl Alcohol | 14.00 |
| Isopropyl Myristate | 1.00 |
| Fragrance | 1.00 |
| Talc | 3.20 |
| Castorwax MP80 | 4.00 |
| Polydecene | — |
|  | 100.00 |
| Total Elastomer Content | 0.0 |

The stick was prepared according to conventional known techniques.

For example, the volatile silicone, stearyl alcohol, and castor wax are melted together in a vessel at a temperature of 65–80° C. with stirring. Other ingredients (e.g. talc, emollient and preservatives) are added slowly with mixing, and subsequently the AAZG is added slowly with stirring, the temperature of the vessel whilst the AAZG is added being kept at around 65° C. Finally, perfume is added to the composition with stirring. The molten composition may then be cast into sticks of the desired shape and cooled.

The resulting stick had a slightly wet, greasy feel.

Example 1

This illustrates an antiperspirant stick product according to the invention. The stick had the following formulation:

|  | wt % |
|---|---|
| Volatile Silicone (DC344) | 27.80 |
| GE Gel | 25.00 |
| AZAG (Active) | 24.00 |
| Stearyl Alcohol | 14.00 |
| Isopropyl Myristate | 1.00 |
| Fragrance | 1.00 |
| Talc | 3.20 |
| Castorwax MP80 | 4.00 |
| Polydecene | — |
|  | 100.00 |
| Total Elastomer Content | 1.25 |

The stick was prepared according to the same method employed in example 1 except that the gel was added with the talc, emollient and preservatives.

A stick according to the above composition had a satisfactory dry feel in use, and acceptable storage properties.

Example 2

An antiperspirant stick having the following formulation was prepared:

|  | wt % |
|---|---|
| Volatile Silicone (DC344) | 40.30 |
| GE Gel | 12.50 |
| AZAG (Active) | 24.00 |
| Stearyl Alcohol | 14.00 |
| Isopropyl Myristate | 1.00 |
| Fragrance | 1.00 |
| Talc | 3.20 |
| Castorwax MP80 | 4.00 |
| Polydecene | — |
|  | 100.00 |
| Total Elastomer Content | 0.625 |

The stick was prepared according to Example 1. The resultant stick had a dry and hard feel.

Example 3

An antiperspirant having the following formulation was prepared:

|  | wt % |
|---|---|
| Volatile Silicone (DC344) | 26.30 |
| GE Gel | 12.50 |
| AZAG (Active) | 24.00 |
| Stearyl Alcohol | 14.00 |
| Isopropyl Myristate | 1.00 |
| Fragrance | 1.00 |
| Talc | 3.20 |
| Castorwax MP80 | 4.00 |
| Polydecene | 14.00 |
|  | 100.00 |
| Total Elastomer Content | 0.625 |

The stick was prepared according to example 1. The resultant stick had a silky/smooth feel, less greasy than the comparative example and low visible deposits. The stick also rubbed in easily. Accordingly, the addition of polydecene further enhanced the cosmetic properties.

We claim:

1. An antiperspirant stick composition suitable for topical application to human skin, comprising:
   i. an effective amount of an antiperspirant astringent;
   ii. a volatile silicone;
   iii. a structurant; and
   iv. a dimethicone/vinyidimethicone cross polymer.

2. A composition according to claim 1 wherein the dimethicone/vinyldimethicone cross polymer is formed from the hydrosilation of vinyl silicone fluids by hydrosiloxane or MQ hydride fluids.

3. An antiperspirant composition according to claim 1 wherein the antiperspirant astringent comprises 5–30% by weight of the composition.

4. An antiperspirant stick composition according to claim 1 further comprising a non-volatile emollient.

5. An antiperspirant stick composition according to claim 4 wherein the non-volatile emollient is a hydrocarbon.

6. An antiperspirant composition according to claim 1 suitable for topical application to the human skin, comprising:
   i. 15–25% by weight of the total composition of an antiperspirant astringent;
   ii. 50–60% by weight of the total composition of a linear or cyclic volatile silicone;
   iii. 5 to 30% by weight of the total composition of long chain water insoluble aliphatic alcohols having 16–22 carbon atoms in the chain; and
   iv. 0.1 to 20% by weight of a vinyldimethicone/ dimethicone cross polymer elastomer.

* * * * *